United States Patent
Montgomery

[19]

[11] Patent Number: 5,816,802
[45] Date of Patent: Oct. 6, 1998

[54] FLEXIBLE DENTAL TRAY

[75] Inventor: Robert E. Montgomery, Monterey, Mass.

[73] Assignees: R. Eric Montgomery; Index Dental Sciences, Inc., both of Monterey, Mass.

[21] Appl. No.: 533,148

[22] Filed: Sep. 25, 1995

[51] Int. Cl.$^6$ .............................. A61C 7/08; A61C 17/00
[52] U.S. Cl. ............................................ 433/80; 128/861
[58] Field of Search ..................... 433/37, 80; 128/861, 128/862

[56] References Cited

U.S. PATENT DOCUMENTS

| | | | |
|---|---|---|---|
| Re. 31,476 | 12/1983 | Mercer | 264/16 |
| 803,475 | 10/1905 | Dennis . | |
| 2,258,883 | 10/1941 | Cressler | 433/80 |
| 2,590,118 | 3/1952 | Oddo, Jr. | 128/861 |
| 3,624,909 | 12/1971 | Greenberg | 433/80 |
| 3,955,281 | 5/1976 | Weitzman | 32/14 |
| 4,044,762 | 8/1977 | Jacobs | 128/136 |
| 4,055,895 | 11/1977 | Huge | 128/861 |
| 4,968,251 | 11/1990 | Darnell | 433/216 |
| 4,983,381 | 1/1991 | Zaragoza | 424/53 |
| 4,990,089 | 2/1991 | Munro | 433/215 |
| 5,018,967 | 5/1991 | Schwalbach | 433/37 |
| 5,032,178 | 7/1991 | Cornell | 106/35 |
| 5,076,791 | 12/1991 | Madray, Jr. | 433/215 |
| 5,082,007 | 1/1992 | Adell | 128/861 |
| 5,165,424 | 11/1992 | Silverman | 128/861 |
| 5,323,787 | 6/1994 | Prah | 433/80 |
| 5,402,066 | 10/1995 | Snyder | 128/861 |

*Primary Examiner*—Paul J. Hirsch
*Attorney, Agent, or Firm*—Bromberg & Sunstein LLP

[57] ABSTRACT

A flexible duplex dental tray such that the upper and the lower teeth can be placed in the upper and the lower dental troughs of the flexible duplex dental tray, respectively. The duplex dental tray is made of an elastic material and is has a radius of curvature less than the dentition of the patient such that the tension created by extending the duplex dental tray when it is worn provides additional support for holding the duplex dental tray in place, in addition to pressure for maintaining contact of tooth bleaching materials contained therein.

10 Claims, 2 Drawing Sheets

FLEXIBLE DENTAL TRAY

BACKGROUND OF THE INVENTION

1. Field of the Invention

This invention relates to dental trays and methods used for applying compositions to teeth.

2. Description of Related Art

Most prior-art dental trays are constructed from rigid or semi-rigid plastic materials and are shaped to define a channel or trough for placement of a dental impression material. Prior-art dental trays typically have a curvature that is intended to approximate the curvature of the intended wearer's dentition. Indeed, since dental trays are often created by molding a cast of the patient's teeth, the curvature of the tray is usually the same as that of the patient's jaw. As a result of the equivalent curvature, when the tray is worn there is very little, if any, elastic tension in the tray which would help push the tray against the patient's teeth. In fact, it was thought that dental impression trays should be equivalent in curvature to the patient's dentition, so as to provide sufficient space between the tray and the tooth surface for impression material to flow. Thus, the dental trays of the prior art did not exert—and were not intended to exert—pressure on the buccal (outer) surface of the teeth when worn by the patient.

SUMMARY OF THE INVENTION

The present invention provides a flexible dental tray that exerts pressure on tooth surfaces when worn by the patient. This pressure, in addition to helping hold the tray in place, enhances the application of a bleaching composition—or other composition, such as a therapeutic composition like fluoride gel—to the tooth surfaces by assuring contact of the tooth surfaces with the composition contained in the tray. Preferably, this dental tray is a duplex tray—i.e., a dental tray that has both an upper tray or trough for the upper teeth and a lower tray or trough for the lower teeth—and has a radius of curvature less than that of the human dentition, such that pressure is exerted by the tray on the buccal (outer) surfaces of the teeth when worn by the patient, thereby holding said tray in place.

In a preferred embodiment, a dental tray that is more curved (has a smaller radius of curvature) than the jaw of the patient. When the tray is placed on the patient's teeth and is therefore stretched into a less curved form (increased radius of curvature), the tray's elasticity (i.e., its resiliency—its natural tendency to go back to its original more curved form) creates a tension which pushes the tray against the patient's teeth thus providing additional support for holding the tray in place. Preferably, a flexible duplex dental tray according to the present invention includes an anterior surface comprising an anterior upper segment and an anterior lower segment; a connector attached to the anterior surface; and a posterior surface attached to the connector and comprising a posterior upper segment and a posterior lower segment. The anterior surface is curved towards the posterior surface while the posterior surface is curved away from the anterior surface. The anterior surface is a predetermined distance away from the posterior surface, such that the anterior upper segment and the posterior upper segment form an upper dental trough, while the anterior lower segment and the posterior lower segment form a lower dental trough. Both the anterior and posterior surfaces possess a radius of curvature less than that of the dentition of the intended patient, or more generally, less than that of a typical adult. Preferably, the anterior surface, the connector and the posterior surface are all comprised of an elastic material.

Preferably, the anterior surface is defined by a first curved ellipse and the posterior surface is defined a second curved ellipse, wherein the first curved ellipse has a greater surface area than the second curved ellipse. The connector is preferably comprised of a connector surface that is substantially perpendicular to the anterior surface and the posterior surface and is bounded by the anterior surface and the posterior surface.

In a preferred method of using the tray, a tooth-bleaching material is deposited within a trough—or preferably both troughs—of the tray. The tray is then placed within the patient's mouth. The tray provides a means for maintaining pressurized contact of said tooth bleaching material against the buccal surfaces of the patient's teeth. The tray may also be used for therapeutically treating teeth by depositing a dentally therapeutic composition within a trough—or preferably both troughs of the tray. The tray is then placed in the patient's mouth,

DESCRIPTION OF THE DRAWINGS

The following drawings are intended to provide a better understanding of the present invention, but they are in no way intended to limit the scope of the invention.

DETAILED DESCRIPTION OF THE INVENTION

Figure 1:
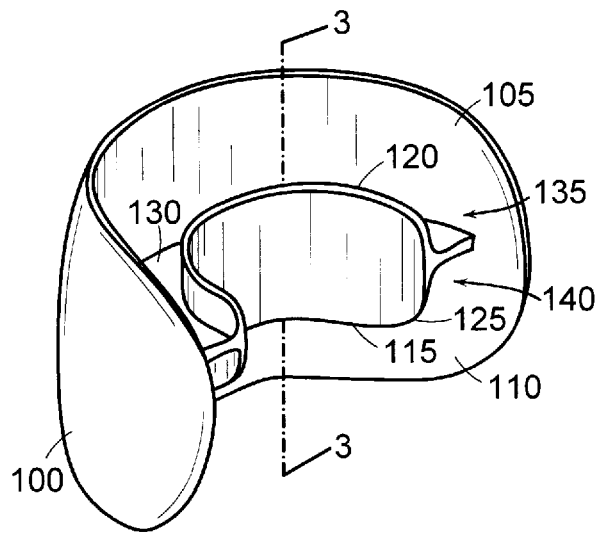
FIG. 1 is a perspective rear view of a duplex dental tray of the present invention.

FIG. 1 is a perspective rear, side view of one preferred embodiment of a duplex dental tray according to the present invention. In FIG. 1, the duplex dental tray is comprised of (i) an anterior curved surface 100, with an upper anterior segment 105 and a lower anterior segment 110, (ii) a posterior curved surface 115, with an upper posterior segment 120 and a lower posterior segment 125, and (iii) a connector 130. The space 135 between the upper anterior segment 105, the upper posterior segment 120 and the connector 130 defines an upper dental tray. The space 140 between the lower anterior segment 110, the lower posterior segment 125 and the connector 130 defines a lower dental tray. The tray is preferably molded from a flexible, resilient thermoplastic material, such as styrene-isoprene-styrene block copolymers or ethylene-vinyl acetate copolymers or other elastomers.

Figure 2:
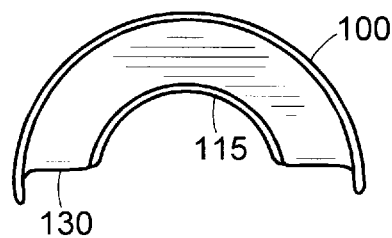
FIG. 2 is the top view of a duplex dental tray of the present invention.

FIG. 2 is the top view (which is a mirror image of the bottom view) of a preferred embodiment of a duplex dental tray of the present invention. As shown in FIG. 2, the anterior curved surface 100 and the posterior curved surface 115 are connected to opposite sides of connector 130. Preferably, the radii of curvature of the anterior and posterior surfaces 100 and 115 are smaller than the radius of curvature of the patient's dentition. Generally, it is preferred that the radius of curvature for each of the two surfaces 100 and 115 be less than the radius of curvature for a typical adult human's dentition; in particular, it is preferred that the radii of curvature for the tray's surfaces 110 and 115 be less than 2.5 centimeters.

Figure 3:
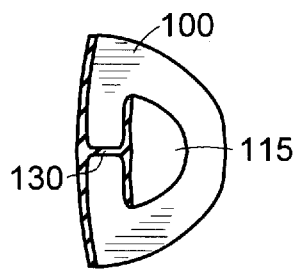
FIG. 3 is a side cross-sectional view of the duplex dental tray of FIG. 1 along line 3—3.
Figure 4:
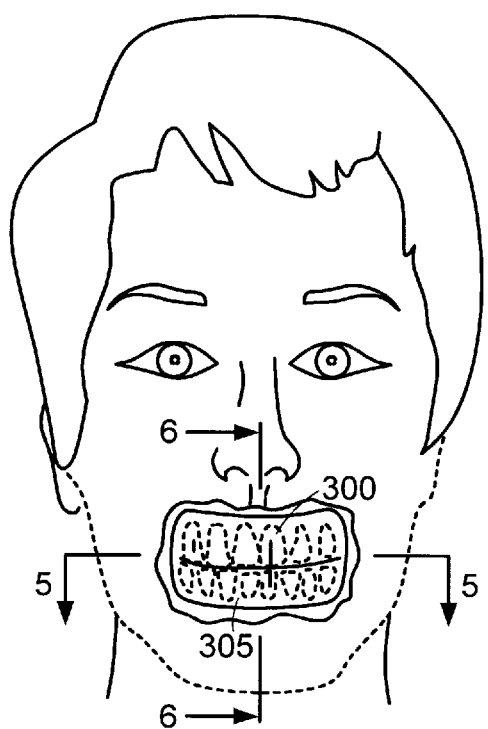
FIG. 4 is a front view of the duplex dental tray of the present invention when worn by a person.

FIG. 3 is a side cross-sectional view of the duplex dental tray of FIG. 1 along line 3—3. FIG. 3 also shows the anterior curved surface 100 and a posterior curved surface 115 being connected to opposite sides of connector 130. FIG. 4 is a front view of the duplex dental tray of the present invention when worn by a person. In FIG. 4, teeth 300 are in the duplex dental tray 305.

Figure 5:
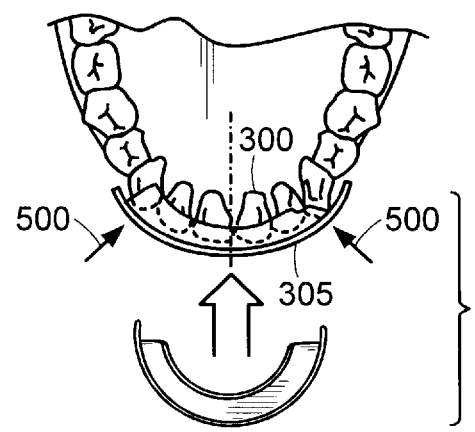
FIG. 5 is a top cross-sectional view of the duplex dental tray of FIG. 4 along line 5—5.

FIG. 5 is a top cross-sectional view of the duplex dental tray of FIG. 4 along line 5—5. FIG. 5 also illustrates the insertion of the duplex dental tray 305 onto the teeth 300. As can be seen in FIG. 5, the duplex dental tray 305 before being placed onto the teeth 300 is curved more than the jaw. Once placed on the teeth 300, the duplex dental tray 305 is bent so as to conform to the curvature of the jaw. The flexing of the duplex dental tray 305 in order to conform it to the curvature of the jaw creates tension at the points indicated by the arrows 500 since the duplex dental tray is elastic and therefore resists the decrease in curvature. The tension created by the tray's elasticity helps support the tray in its position when worn as the tension pushes the tray against the patient's teeth. This tension also ensures contact of the buccal tooth surfaces with the composition placed in the upper and lower dental trays.

Figure 6:
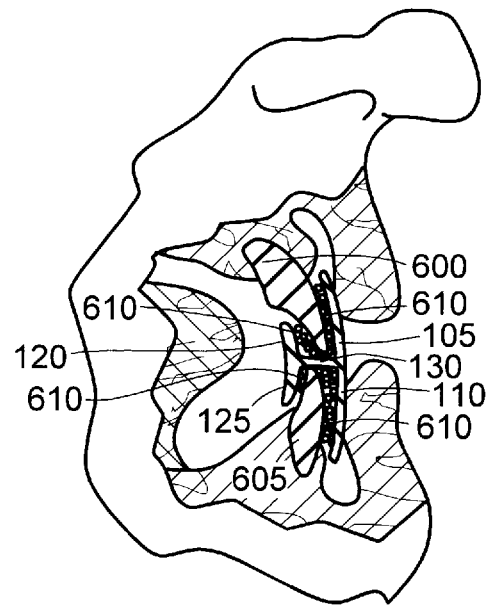
FIG. 6 is a side cross-sectional view of the duplex dental tray of FIG. 4 along line 6—6.

FIG. 6 is a side cross-sectional view of the duplex dental tray of FIG. 4 along line 6—6. In FIG. 6, tooth 600 is in the upper dental tray of the duplex dental tray which is defined by the upper anterior segment 105, the upper posterior segment 120 and the connector 130. Tooth 605 is in the lower dental tray of the duplex dental tray which is defined by the lower anterior segment 110, the lower posterior segment 125 and the connector 130. The bleaching agent 610, which is preferably a peroxide gel (such as, for example, the peroxide gel described in U.S. Pat. No. 5,290,566, or alternatively a composition described in concurrently filed provisional application entitled "Improved Method of Whitening Teeth" for an invention by Robert E. Montgomery and bearing attorney docket number 1910/110) occupies the space between the teeth and the duplex dental tray.

Also contemplated to be within the scope of the present invention is the use of the flexible tray as a reservoir for dentally therapeutic compositions, such as fluoride gels.

The above description of the drawings provides details of the preferred embodiment of the present invention. It is of course apparent that the present invention is not limited to the detailed description set forth above. Various changes and modifications of this invention as described will be apparent to those skilled in the art without departing from the spirit and scope of this invention as defined in the following claims.

What is claimed is:

1. A method of bleaching teeth of a user comprising:
   providing a dental tray having two surfaces, each surface having a radius of curvature different from that of a dentition of the user, and a connector joining the two surfaces, wherein the connector and the surfaces are integrally molded to define an upper trough and a lower trough, each with a radius of curvature different from that of the dentition of the user, so that, when the tray is inserted into the user's mouth, the surfaces apply pressure against tooth surfaces of the user;
   depositing a tooth bleaching composition within the upper and lower troughs of the tray; and
   placing the tray and bleaching composition in the user's mouth.

2. A method as set forth in claim 1, wherein in the step of providing, the radius of curvature of each of the upper and lower troughs is smaller than that of the dentition of the user.

3. A method of therapeutically treating teeth of a user comprising:
   providing a dental tray having two surfaces, each surface having a radius of curvature different from that of a dentition of the user, and a connector joining the two surfaces, wherein the connector and the surfaces are integrally molded to define an upper trough and a lower trough, each with a radius of curvature different from that of the dentition of the user, so that, when the tray is inserted into the user's mouth, the surfaces apply pressure against tooth surfaces of the user;
   depositing a dentally therapeutic composition within the upper and lower troughs of the tray; and
   placing the tray and dentally therapeutic composition in a patient's mouth.

4. A method as set forth in claim 3, wherein in the step of providing, the radius of curvature of each of the upper and lower troughs is smaller than that of the dentition of the user.

5. A method of bleaching teeth comprising:
   (a) providing a flexible duplex tray having:
      an anterior surface having a radius of curvature smaller than that of the dentition of a patient and comprising an anterior upper segment and an anterior lower segment;
      a posterior surface having a radius of curvature smaller than that of the dentition of the intended patient and comprising a posterior upper segment and a posterior lower segment; and
      a connector integrally molded with the anterior and posterior surfaces;
      wherein the anterior surface is curved towards the posterior surface while the posterior surface is curved away from the anterior surface and further wherein the anterior surface is spaced a distance away from the posterior surface, such that the anterior upper segment and the posterior upper segment form an upper dental trough, while the anterior lower segment and the posterior lower segment form a lower dental trough;
   (b) depositing a tooth bleaching composition within both the upper and lower dental troughs of the flexible duplex tray; and
   (c) placing said flexible duplex tray and bleaching composition in a patient's mouth.

6. A method of therapeutically treating teeth comprising:
   (a) providing a flexible duplex tray having:
      an anterior surface having a radius of curvature smaller than that of the dentition of a patient and comprising an anterior upper segment and an anterior lower segment;
      a posterior surface having a radius of curvature smaller than that of the dentition of the intended patient and comprising a posterior upper segment and a posterior lower segment; and
      a connector integrally molded with the anterior and posterior surfaces;
      wherein the anterior surface is curved towards the posterior surface while the posterior surface is curved away from the anterior surface and further wherein the anterior surface is spaced a distance away from the posterior surface, such that the anterior upper segment and the posterior upper segment form an upper dental trough, while the anterior lower segment and the posterior lower segment form a lower dental trough;

(b) depositing a dentally therapeutic composition within both the upper and lower dental troughs of the flexible duplex tray; and (c) placing said flexible duplex tray and dentally therapeutic composition in a patient's mouth.

7. A method of bleaching teeth of a user comprising:

providing a dental tray integrally molded from a resilient, flexible thermoplastic material and defining an upper trough and a lower trough, each having an anterior portion and a posterior portion, each portion having a radius of curvature different from that of the dentition of the user, such that when the tray is inserted into the user's mouth, the portions apply pressure against tooth surfaces of the user;

depositing a tooth bleaching composition within the upper and lower troughs of the tray; and placing the tray and bleaching composition in the user's mouth.

8. A method of therapeutically treating teeth of a user comprising:

providing a dental tray integrally molded from a resilient, flexible thermoplastic material and defining an upper trough and a lower trough, each having an anterior portion and a posterior portion, each portion having a radius of curvature different from that of the dentition of the user, such that when the tray is inserted into the user's mouth, the portions apply pressure against tooth surfaces of the user;

depositing a dentally therapeutic composition within the upper and lower troughs of the tray; and placing the tray and dentally therapeutic composition in a patient's mouth.

9. A method of bleaching teeth comprising:

(a) providing a flexible duplex tray having:

an anterior surface having a radius of curvature different than that of the dentition of a user and comprising an anterior upper segment and an anterior lower segment;

a posterior surface having a radius of curvature smaller than that of the dentition of the user and comprising a posterior upper segment and a posterior lower segment; and a connector joining the anterior and posterior surfaces and having a width larger than that of the dentition of the user;

wherein the anterior surface is curved towards the posterior surface while the posterior surface is curved away from the anterior surface and further wherein the anterior surface is spaced from the posterior surface by a distance of the width of the connector, such that the anterior upper segment and the posterior upper segment form an upper dental trough, while the anterior lower segment and the posterior lower segment form a lower dental trough;

(b) depositing a tooth bleaching composition within both the upper and lower dental troughs of the flexible duplex tray; and (c) placing said flexible duplex tray and bleaching composition in a patient's mouth.

10. A method of therapeutically treating teeth comprising:

(a) providing a flexible duplex tray having:

an anterior surface having a radius of curvature different than that of the dentition of a user and comprising an anterior upper segment and an anterior lower segment;

a posterior surface having a radius of curvature smaller than that of the dentition of the user and comprising a posterior upper segment and a posterior lower segment; and a connector joining the anterior and posterior surfaces and having a width larger than that of the dentition of the user;

wherein the anterior surface is curved towards the posterior surface while the posterior surface is curved away from the anterior surface and further wherein the anterior surface is spaced from the posterior surface by a distance of the width of the connector, such that the anterior upper segment and the posterior upper segment form an upper dental trough, while the anterior lower segment and the posterior lower segment form a lower dental trough;

(b) depositing a dentally therapeutic composition within both the upper and lower dental troughs of the flexible duplex tray; and (c) placing said flexible duplex tray and dentally therapeutic composition in a patient's mouth.

* * * * *

UNITED STATES PATENT AND TRADEMARK OFFICE
CERTIFICATE OF CORRECTION

PATENT NO. : 5,816,802
DATED : October 6, 1998
INVENTOR(S) : Montgomery

It is certified that error appears in the above-identified patent and that said Letters Patent is hereby corrected as shown below:

On the title page, item [73] should read:

Assignees: R. Eric Montgomery; Idex Dental Sciences, Inc., both of Monterey, Mass.

Signed and Sealed this

Second Day of February, 1999

Attest:

Attesting Officer

*Acting Commissioner of Patents and Trademarks*